US005110586A

United States Patent [19]

Kurihara et al.

[11] Patent Number: 5,110,586

[45] Date of Patent: May 5, 1992

[54] WHITE COLORED DEODORIZER AND PROCESS FOR PRODUCING THE SAME

[75] Inventors: Tokumitsu Kurihara; Tatsuo Saito; Hidefumi Harada, all of Yamaguchi, Japan

[73] Assignee: Titan Kogyo Kabushiki Kaisha, Ube, Japan

[21] Appl. No.: 541,074

[22] Filed: Jun. 21, 1990

Related U.S. Application Data

[63] Continuation of Ser. No. 238,459, Aug. 30, 1988, abandoned.

[51] Int. Cl.[5] .............................................. A41B 13/02

[52] U.S. Cl. .................................. 424/76.1; 106/426; 106/431; 423/339; 423/622; 423/625; 424/76.5; 424/76.7

[58] Field of Search ....................... 423/339, 622, 625; 424/76.1, 76.5, 76.7; 106/426, 431

[56] References Cited

U.S. PATENT DOCUMENTS

| | | | |
|---|---|---|---|
| 2,350,047 | 9/1941 | Klarmann et al. | 424/68 |
| 3,028,250 | 4/1962 | Dunn | 106/426 |
| 3,383,231 | 5/1968 | Allan | 106/430 |
| 3,961,037 | 6/1976 | Davies et al. | 423/656 |
| 4,088,736 | 5/1978 | Courty et al. | 423/230 |
| 4,128,630 | 12/1978 | Hayashi et al. | 424/69 |
| 4,297,233 | 10/1981 | Gualandi | 252/259.5 |
| 4,414,200 | 11/1983 | Murphy et al. | 424/63 |
| 4,440,668 | 3/1984 | Chang et al. | 502/331 |
| 4,492,769 | 1/1985 | Blanchard et al. | 502/262 |
| 4,677,096 | 6/1987 | Van der Smissen | 502/415 |
| 4,777,034 | 8/1988 | Oliver et al. | 424/65 |

FOREIGN PATENT DOCUMENTS

| | | |
|---|---|---|
| 5061926 | 5/1980 | Japan . |
| 1209030 | 9/1986 | Japan . |
| WO81/01643 | 6/1981 | PCT Int'l Appl. . |

*Primary Examiner*—Ellis P. Robinson
*Assistant Examiner*—Archene Turner
*Attorney, Agent, or Firm*—Fitch, Even, Tabin & Flannery

[57] ABSTRACT

A white colored deodorizer comprising zinc oxide and at least one oxide selected from the group consisting of aluminium oxide and silicon oxide and a method for preparation of it are disclosed.

2 Claims, No Drawings

WHITE COLORED DEODORIZER AND PROCESS FOR PRODUCING THE SAME

This application is a continuation of application Ser. No. 238,459 filed Aug. 30, 1988, now abandoned.

BACKGROUND OF THE INVENTION

The present invention relates to an agent for reducing the levels of odorous gases such as ammonia, mercaptans, amines and aldehydes. More specifically, the present invention relates to a novel deodorizer in white particulate form that contains as main ingredients zinc oxide and at least one oxide (hereinunder referred to as oxide A) selected from the group consisting of aluminium oxide, silicon dioxide and mixtures thereof and which has very good adsorption characteristics.

Hydrogen sulfide, ammonia, mercaptans, amines, aldehydes and other odorous gases that are generated in daily life have caused an increasing amount of social concern about the deleterious effects they have on the biosphere and environment. In response to these concerns, a variety of deodorizers that are capable of reducing the target odorous gases have been proposed and put to practical use. Deodorizers for use in daily life have to satisfy the following minimal requirements:

(1) they must be capable of efficient reduction of the levels of hydrogen sulfide, ammonia, mercaptans, amines, aldehydes and other odorous gases that are generated in daily life;
(2) they must be safe to use;
(3) they must be easy to handle;
(4) they must be inexpensive; and
(5) they must offer a feeling of cleanliness.

However, none of the conventional deodorizers satisfy all of these requirements, nor do the most recently developed products. Activated carbon which is the most popular deodorizer in use today is highly effective in reducing mercaptans and amines but is not equally effective against hydrogen sulfide and ammonia which are typical of the odorous gases that are generated in daily life. In an attempt to solve this problem, a product has been developed that has an acid, an alkali or a certain halide supported on activated carbon. However, because of the use of an acid or alkali, this product requires very careful handling to avoid any danger to humans and hence is not suitable for daily use. Furthermore, the inherent black color of activated carbon limits the scope of use of deodorizers based on activated carbon.

Iron sulfate ($FeSO_4$) having L-ascorbic acid bound thereto is effective against basic odorous gases such as ammonia and amines but is little effective in reducing hydrogen sulfide, mercaptans and aldehydes. Furthermore, this product dissolves in water and hence is not suitable for the purpose of deodorizing wet gases.

Deodorizers classified as chemical odor modifiers are also available but many of them have strong acidity or alkalinity and the kinds of odorous gases that can be effectively controlled by these odor modifiers are limited. In addition, such deodorizers are sensitive to moisture and/or a dry atmosphere.

Organic deodorizers have low heat resistance, are difficult to process, and are expensive.

SUMMARY OF THE INVENTION

It is accordingly an object of the present invention to provide a novel deodorizer that is highly effective in reducing odorous gases generated in daily life such as ammonia, mercaptans, amines and aldehydes and which are safe and easy to handle.

This object of the present invention can be attained by a white colored deodorizer which is a white fine powder comprising coagulated particles of zinc oxide and oxide A.

DETAILED DESCRIPTION OF THE INVENTION

The deodorizer of the present invention may be produced by the following procedures. A mixed aqueous solution of a water-soluble zinc compound and at least one compound selected from the group consisting of water-soluble aluminium compounds, water-soluble silicon compounds and mixtures thereof is mixed with an alkaline aqueous solution or an acidic aqueous solution by simultaneous addition into a certain medium in such a way that the combined solution will have a final pH of at least 6, preferably 6-12, thereby forming a white precipitate in the combined solution that is composed of zinc oxide and oxide A. In the next step, the precipitate is separated from the combined solution and dried.

Examples of the water-soluble zinc compounds that can be used as a starting material for the production of the deodorizer of the present invention include zinc sulfate, zinc chloride and zinc nitrate. Examples of suitable water-soluble aluminium compounds include aluminium sulfate, aluminium chloride and sodium aluminate. Illustrative water-soluble silicon compounds include sodium silicate and potassium silicate.

Almost any acid aqueous solution can be used for neutralizing the mixed aqueous solution, for example, sulfuric acid, hydrochloric acid, etc. The alkaline aqueous solution used for neutralizing the mixed aqueous solution may be selected from among aqueous solutions of an alkaline metal hydroxide such as sodium hydroxide and potassium hydroxide, an alkaline earth metal hydroxide such as calcium hydroxide and barium hydroxide and an ammonia. If a sulfate is used as a zinc compound or an aluminium compound, aqueous solutions of calcium hydroxide and barium hydroxide are not desirably used since they will produce water-insoluble salts.

The water-soluble zinc compound and at least one compound selected from the group consisting of water-soluble aluminium compounds, water-soluble silicon compounds and mixtures thereof are mixed in such proportions that the molar ratio of zinc oxide to oxide A is within the range of 5:95 to 95:5. If the molar ratio of zinc oxide to oxide A is smaller than 5:95 or greater than 95:5, the fine powder prepared from the resulting precipitate will display absorption characteristics similar to either pure aluminium oxide, silicon dioxide or pure zinc oxide. These characteristics are substantially inferior to those of the fine powder obtained in accordance with the compositional range specified by the present invention.

Zinc oxide precipitate at a pH range of 6-14, and an aluminium oxide and a silicon dioxide precipitate at a pH range of 4-12 and 0-12. Accordingly, a precipitate of intended composition is formed by keeping the pH of the mixed solution between 6 and 12. If the aqueous solution contains ammonia, it is preferable that the pH of the aqueous solution is kept between 7 and 9, because zinc will make a complex salt with ammonia and will be soluble in the aqueous solution at high pH.

For the purposes of the present invention, it is essential that the mixed aqueous solution and the aqueous alkaline solution or the aqueous acidic solution be mixed together in such a way that the resulting combined solution will keep its pH between 6 and 12. If the alkaline aqueous solution or the aqueous acidic solution is added to the mixed aqueous solution gradually over a certain period of time until the combined solution has a final pH between 6 and 12, and the combined solution does not keep its pH between 6 and 12 during the addition of alkaline solution or acidic solution, the finally obtained product will not have the intended composition.

When the mixed aqueous solution and the alkaline aqueous solution are mixed together to form a precipitate composed of zinc oxide and oxide A, a temperature in the range of 20°-80° C. may be employed, with the range of 40° C.-60° C. being preferred.

After the precipitate has been filtered and washed, it may be dried at a temperature in the range of 100° C.-350° C., preferably 120° C.-250° C. The deodorizer of the present invention which contains as essential ingredients zinc oxide and oxide A will maintain satisfactory adsorption characteristics even if it is heated up to 400° C.

The white-colored deodorizer of the present invention which is based on the combination of zinc oxide and oxide A is capable of efficient reduction in the levels of hydrogen sulfide, ammonia, amines and other odorous gases that are generated in daily life. In addition, this deodorizer is safe to use since the zinc oxide and oxide A that are incorporated are nontoxic. Furthermore, the deodorizer is in a fine particulate form and can be readily supported on a carrier such as paper or other sheet materials. The deodorizer is thermally stable up to about 400° C. and can be worked into conventional plastics. In addition to the high potential of its industrial utility, the deodorizer of the present invention which is white in color is also suitable for use in cosmetics, sanitary products and disposable diapers.

The following examples are provided for the purpose of further illustrating the present invention but are not to be taken as limiting the scope thereof.

EXAMPLE 1

A 5-l beaker was charged with 1 l of pure water, which was heated at 60° C. with stirring. A mixed aqueous solution (2 l) of zinc sulfate (81.37 g as zinc oxide) and aluminum sulfate (50.98 g as aluminium oxide) and an aqueous ammonia solution were simultaneously added dropwise to the pure water in the beaker over a period of 30 minutes with care being taken to ensure that the pH of the combined solution remained at 7.5. The resulting product was filtered, washed and dried at 120° C. for 6 hours to produce a white deodorizer of the zinc oxide—aluminium oxide within the scope of the present invention.

The ability of this white deodorizer to adsorb odorous gases (i.e., hydrogen sulfide, ammonia, trimethylamine and ethyl mercaptan) was investigated by the following method. The white powder of the deodorizer (100 mg) was put into a glass vial having an inner capacity of 120 ml. After closing the vial with a rubber stopper, predetermined amounts of certain odorous gases were injected into the vial with a microsyringe. Two hours after the gas injection, the air in the vial was sampled with a microsyringe and the concentrations of the odorous gases in it were measured by gas chromatography. The results are shown in Table 1.

EXAMPLE 2

A white deodorizer of the zinc oxide—aluminium oxide system was prepared by repeating the procedures of Example 1 except that a mixed aqueous solution of zinc sulfate (81.37 g as zinc oxide) and aluminium sulfate (25.49 g as aluminium oxide) was used. The adsorption characteristics of the prepared deodorizer for various odorous gases are shown in Table 1.

EXAMPLE 3

A 5-l beaker was charged with 1 l of pure water, which was heated at 60° C. with stirring. A mixed aqueous solution (1 l) of zinc chloride (122.05 g as zinc oxide), sodium aluminate (25.49 g as aluminium oxide) and an sodium hydroxide were simultaneously added dropwise to the pure water in the beaker over a period of 30 minutes with care being taken to ensure that the pH of the combined solution remained at 7.5. The resulting product was filtered, washed and dried at 120° C. for 6 hours to produce a white deodorizer.

EXAMPLE 4

A white deodorizer was prepared by repeating the procedures of Example 3 except that the sodium aluminate was replaced by an aqueous solution of sodium silicate (30.04 g as silicon oxide).

EXAMPLE 5

A white deodorizer was prepared by repeating the procedures of Example 4 except that the aqueous solution of zinc chloride was replaced by a mixed aqueous solution of zinc chloride (81.37 g as zinc oxide) and aluminium chloride (50.98 g as aluminium oxide).

TABLE 1

| | | Gas concentration (ppm) after 30 min of adsorption | | | |
|---|---|---|---|---|---|
| | Composition (molar ratio) | Ammonia 1000* | Hydrogen sulfide 1000* | Ethyl mercaptan 1000* | Trimethyl amine 1000* |
| Example 1 | $ZnO:Al_2O_3 = 2:1$ | 30 | 0 | 5 | 20 |
| Example 2 | $ZnO:Al_2O_3 = 4:1$ | 10 | 0 | 2 | 30 |
| Example 3 | $ZnO:Al_2O_3 = 6:1$ | 5 | 0 | 0 | 10 |
| Example 4 | $ZnO:SiO_2 = 3:1$ | 0 | 0 | 0 | 10 |
| Example 5 | $ZnO:SiO_2:Al_2O_3 = 2:1:1$ | 10 | 0 | 5 | 10 |

*Initial concentrations in ppm.

What is claimed is:

1. A process for producing a white colored deodorizer consisting essentially of the steps of:

combining an aqueous alkaline solution or an aqueous acidic solution with a mixed aqueous solution containing a water-soluble zinc compound and at least one compound selected from the group consisting of water-soluble aluminum compounds, water-soluble silicon compounds and mixtures thereof, said combining step being performed by simultaneous addition of the two solutions in such a way that the combined solution will keep its pH in the range of 6 to 12 and said combining step is performed at a temperature of 20° C. to 80° C. to form a precipitate;

separating the precipitate from the combined solution; and drying the separated precipitate at 120° C. to 350° C. to form a white fine powder consisting essentially of zinc oxide and at least one oxide selected from the group consisting of aluminum oxide, silicon dioxide and mixtures thereof, wherein the molar ratio of zinc oxide to oxide is in the range of from 5:95 to 95:5.

2. A process according to claim 1 wherein the molar ratio of zinc oxide to oxide is in the range of from 40:60 to 90:10.

* * * * *

UNITED STATES PATENT AND TRADEMARK OFFICE

CERTIFICATE OF CORRECTION

PATENT NO. : 5,110,586

DATED : May 5, 1992

INVENTOR(S) : Kurihari et al.

It is certified that error appears in the above-identified patent and that said Letters Patent is hereby corrected as shown below:

Item [57] ABSTRACT, line 3, change "silicon oxide" to --silicon dioxide--.

Column 2, line 60, after "Zinc oxide" change "precipitate" to --precipitates--.

Column 3, line 46, change "5-1" to --5-l (liter)--; and change "1 1" to --1 l (liter)--.

Column 3, line 48, change "(2 1)" to --(2 l) (liter)--.

Column 4, line 26, change "5-1" to --5-l (liter)--; and change "1 1" to --1 l (liter)--.

Column 4, line 28, change "(1 1)" to --(1 l) (liter)--.

Column 4, line 30, delete "an".

Signed and Sealed this

Twenty-fourth Day of August, 1993

Attest:

BRUCE LEHMAN

*Attesting Officer* — *Commissioner of Patents and Trademarks*